United States Patent [19]

Wollweber et al.

[11] Patent Number: 4,935,409
[45] Date of Patent: Jun. 19, 1990

[54] AMINOPHENYLETHYLAMINE YIELD PROMOTERS

[75] Inventors: Hartmund Wollweber, Wuppertal; Jürgen Stoltefuss, Haan; Friedrich Berschauer, Wuppertal, all of Fed. Rep. of Germany

[73] Assignee: Bayer Aktiengesellschaft, Leverkusen, Fed. Rep. of Germany

[21] Appl. No.: 186,522

[22] Filed: Apr. 27, 1988

[30] Foreign Application Priority Data

Apr. 30, 1987 [DE] Fed. Rep. of Germany ....... 3714484

[51] Int. Cl.$^5$ .......................................... C07C 149/36
[52] U.S. Cl. ....................................... 514/63; 514/449; 514/451; 514/459; 514/532; 514/534; 514/543; 514/544; 514/546; 514/646; 556/489; 558/414; 558/418; 560/8; 560/45; 560/129; 564/346; 564/363
[58] Field of Search ................ 564/363, 346; 549/214, 549/426, 491, 494, 495; 556/489, 414, 418; 560/8, 45, 129; 514/63, 449, 451, 459, 532, 534, 543, 544, 546, 646

[56] References Cited

U.S. PATENT DOCUMENTS 3,536,712 10/1970 Keck .................................. 564/363
3,574,211 4/1971 Keck .................................. 564/363

FOREIGN PATENT DOCUMENTS 0026298 9/1980 European Pat. Off. .
0119446 9/1984 European Pat. Off. .
0181709 5/1986 European Pat. Off. .
2354959 5/1975 Fed. Rep. of Germany .

OTHER PUBLICATIONS

Arzneimittel Forschung/Drug Research, vol. 34, No. 11a, 1984, pp. 1612–1624, Aulendorf, DE; G. Kruger et al.: "Synthesis of Further Amino–Halogen–Substituted Phenyl–Aminoethanols"; pp. 1614, 1615, Tabelle 1.
B. R. E. Lutz and co-workers, J. Org. Chem. 12, 617–703.

Primary Examiner—Richard L. Raymond
Assistant Examiner—Raymond Covington
Attorney, Agent, or Firm—Sprung Horn Kramer & Woods

[57] ABSTRACT

Animal growth promoters of the formula

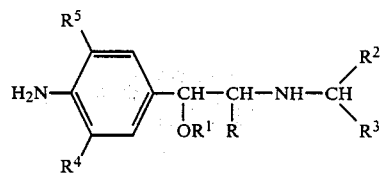

(I)

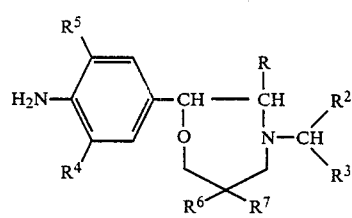

(Ia)

or

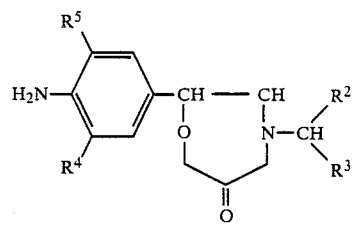

(Ib)

The intermediates of the formula

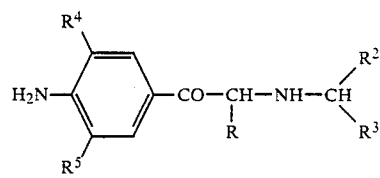

are also new.

6 Claims, No Drawings

AMINOPHENYLETHYLAMINE YIELD PROMOTERS

The present invention relates to new aminophenylethylamine derivatives, to processes for their preparation and to their use as yield promoters for animals.

The use of feed additives to achieve higher increases in weight and improved feed utilization is already practised widely in animal nutrition, in particular in the fattening of pigs, cattle and poultry. It is known that substituted arylethanolamines promote the weight increase of animals (European Published Specification 26,298). However, their action is not satisfactory in all cases.

The new compounds of the general formula

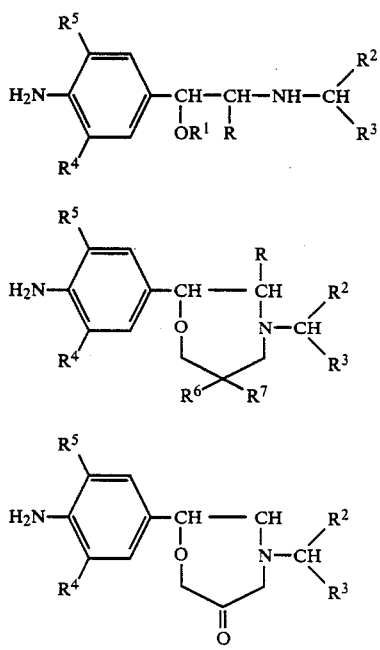

in which
R = H or alkyl,
$R^1$ = hydrogen, acyl, aroyl, arylacyl or

$R^2$ = methyl or ethyl,
$R^3$ = straight-chain, branched or cyclic alkyl which is substituted by alkoxy or alkylthio or heterocyclyl which has 4–6 ring atoms and oxygen as the hetero atom and is optionally substituted by alkyl,
$R^4$ = H, alkyl ($C_1$-$C_3$), halogen, trifluoromethyl or CN,
$R^5$ = alkyl ($C_1$-$C_3$), halogen, trifluoromethyl, CN, alkoxy or alkylthio,
$R^6$ = H or alkyl,
$R^7$ = H, alkyl, phenyl or phenylalkyl and
$R^8$, $R^9$ and $R^{10}$ = a straight-chain or branched alkyl radical,
and their physiologically tolerated salts have been found. The compounds according to the invention can exist in the form of their racemates and their enantiomers or diastereomers.

They have an excellent yield-promoting, in particular growth-promoting, action on animals, for example they effect a shift in the meat/fat ratio in favor of meat.

Preferred compounds are phenylethylamine derivatives of the general formula (I)
in which
R = hydrogen or methyl and
$R^1$ = hydrogen or the radicals —Si(CH$_3$)$_2$CH(CH$_3$)CH(CH$_3$)$_2$ or Si(CH$_3$)$_2$C(CH$_3$)$_3$,
$R^2$ = methyl,
$R^3$ represents the radical $(CR^{11}R^{12})_n$—X—$R^{13}$,
wherein
$R^{11}$ and $R^{12}$ represent hydrogen or methyl or
$R^3$ represents $C_{5-6}$-cycloalkyl which is substituted by $C_{1-4}$-alkoxy,
n represents 1, 2 or 3 and
$R^{13}$ represents $C_{1-4}$-alkyl or, together with one of the radicals $R^{11}$ or $R^{12}$ and the atoms to which they are bonded, forms a 4- to 6-membered ring which is interrupted by O and is optionally substituted by methyl.

Especially preferred compounds of the formula I are those
in which the radical NH—CH(R$^2$)(R$^3$) represents the following radicals:

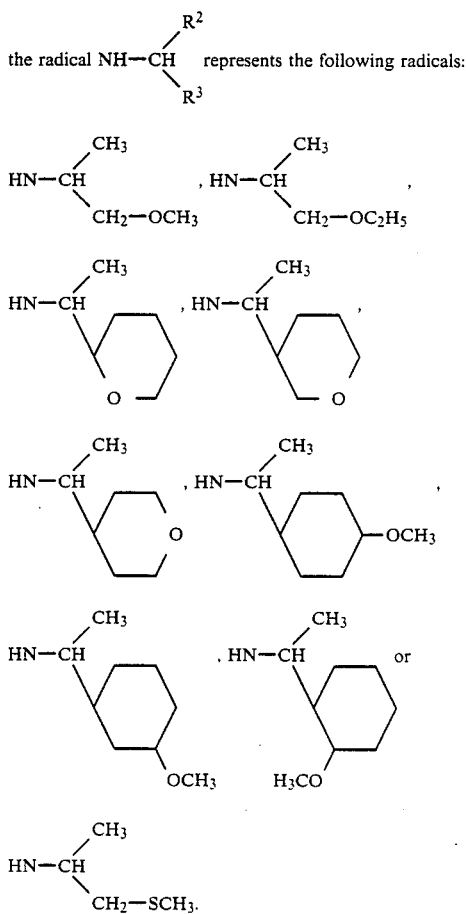

The new compounds of the formula (I)

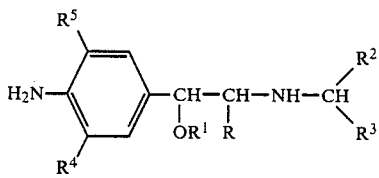 (I)

in which
R and $R^2$ to $R^5$ have the abovementioned meanings and
$R^1$ represents hydrogen, are obtained by a process in which
(a) compounds of the formula (II)

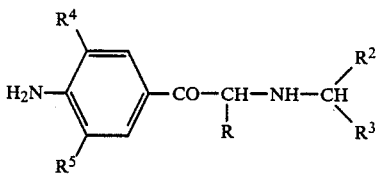 (II)

in which
R and $R^2$ to $R^5$ have the abovementioned meanings, are reduced catalytically or with suitable reducing agents, such as, for example, sodium borohydride, sodium cyanoborohydride and the like, or
(b) compounds of the formula (III)

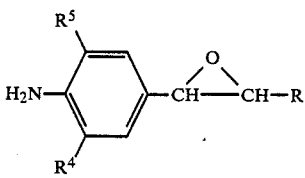 (III)

in which
R, $R^4$ and $R^5$ have the abovementioned meanings, are reacted with amines of the formula (IV)

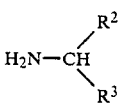 (IV)

in which
R, $R^2$ and $R^3$ have the abovementioned meanings, or
(c) in the case of compounds of the formula (I)
in which
R represents hydrogen and
$R^1$ has the abovementioned meaning,
by a process in which compounds of the formula (V)

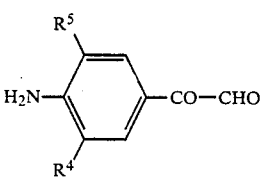 (V)

in which
$R^4$ and $R^5$ have the abovementioned meanings, are reacted with an amine of the formula (IV) in the presence of a reducing agent, such as, for example, sodium borohydride.
(d) The new compounds of the formula (I)
in which
R and $R^2$-$R^5$ have the meanings given in the case of (I) and
$R^1$ represents the radical

and
$R^8$, $R^9$ and $R^{10}$ have the aforementioned meanings, are obtained by a process in which compounds of the formula (I)
in which
$R^1$ represents hydrogen, are reacted with suitable silylating substances of the formula (VI)

$$R^8 R^9 R^{10} Si\ Z \qquad (VI)$$

in which
Z represents halogen, CN, $OSO_2$—$CF_3$, —O—Si—$R^2R^3R^4$ or —O—$SO_2$—O—Si—$R^8R^9R^{10}$ and
$R^8$, $R^9$ and $R^{10}$ have the abovementioned meanings, or
(e) the compound of the formula (III) (above) is reacted with a silylated amine of the formula (VII)

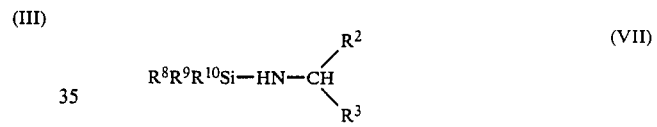 (VII)

in which
$R^8$, $R^9$ and $R^{10}$ have the abovementioned meanings.
(f) The new compounds of the formula (I)
in which
R and $R^2$-$R^5$ have the meanings given in the case of (I) and
$R^1$ represents acyl, aroyl or arylacyl, are obtained by a process in which the compounds of the formula (I)
in which
$R^1$ represents hydrogen,
are reacted with suitable acylating agents, or
(g) the compounds of the formula (Ia)
in which
$R^2$-$R^7$ have the meanings given in the case of (I),
are obtained by a process in which the compounds of the formula (I)
in which
$r^1$ represents hydrogen,
are reacted with carbonyl compounds of the formula

in which
$R^6$ and $R^7$ have the abovementioned meanings, if appropriate in the presence of acid catalysts, or
(h) compounds of the formula (Ib)
in which $R^2$–$R^5$ have the abovementioned meanings,
are obtained by a process in which compounds of the formula (I)
in which
$R^1$ represents hydrogen,
are cyclized with carbonic acid derivatives, if appropriate in the presence of bases.

The starting compounds of the formula (III) and (V) are already known (compare, for example, B. R. E. Lutz and co-workers, J. Org. Chem. 12, 617–703 and DAS (German Published Specification) 2,354,959). The compounds of the formula (II) are new but can be prepared by known methods (compare J. Org. Chem. 12, 617–703). The amines of the formula (IV) are known or can be prepared by known methods by amination of corresponding ketones.

Processes (a)–(h) are carried out analogously to known methods of organic chemistry.

Processes (a)–(h) according to the invention can be carried out in the presence of diluents. Possible diluents are all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl ether, dibutyl ether, glycol dimethyl ether, diglycol dimethyl ether, tetrahydrofuran and dioxane, and moreover ketones, such as acetone, methyl ethyl ketone, methyl isopropyl ketone and methyl isobutyl ketone, and also esters, such as methyl and ethyl acetate, and furthermore nitriles, such as, for example, acetonitrile, propionitrile, benzonitrile and glutaric acid dinitrile, and moreover amides, such as, for example, dimethylformamide, dimethylacetamide and N-methylpyrrolidone, as well as dimethylsulphoxide, tetramethylenesulphone and hexamethylphosphoric acid triamide.

Process (d) according to the invention can be carried out in the presence of catalysts. Catalysts which can preferably be used are: imidazole, triazole or diisopropylethylamine.

The reaction temperature in processes (a)–(h) is kept between about 0° C. and 130° C., preferably between about 20° C. and 60° C. The processes are preferably carried out at atmospheric pressure.

In process (e), the starting compounds of the formulae II and IV are in general employed in an approximately equimolar ratio, but an excess of up to 300% of the compounds of the formula IV can be employed.

In the other processes, the starting compounds are in general employed in an approximately equimolar ratio. The reducing agents can be used in a 1- to 10-fold excess.

The active compounds have a favorable toxicity towards warm-blooded animals and are suitable as agents for yield promotion in animals for breeding and stock animals. They are used here for promoting and accelerating growth and milk and wool production and for improving the feed utilization and meat quality and for shifting the meat-fat ratio in favor of meat.

The stock animals and animals for breeding include mammals, such as, for example, cattle, horses, sheep, pigs, goats, camels, water buffalo, asses, rabbits, fallow deer and reindeer, fur-bearing animals, such as, for example, mink, chinchillas and racoons, birds, such as, for example, chickens, geese, turkeys and ducks, and freshwater and saltwater fish, such as, for example, trout, carp and eels.

The active compounds are used throughout all the growth and yield phases of the animals, regardless of the sex of the animals. The active compounds are preferably used during the intensive growth and yield phase. The intensive growth and yield phase lasts from one month to 10 years, depending on the species of animal.

The compounds according to the invention moreover exhibit a good-anti-inflammatory action on the carrageenan-induced paw oedema in rats.

They can therefore be used as anti-inflammatories and antirheumatics and for the treatment of inflammation and oedemas.

The active compounds have proved to be particularly useful in the rearing and keeping of young animals and fattening animals.

The active compounds are used enterally or parenterally, directly or in the form of formulations suitable for animals. Enteral use of the active compounds is effected, for example, orally in the form of powders, tablets, capsules, pastes, drinks or granules, solutions, emulsions or suspensions for oral administration, or boli, or via the feed or the drinking water. Parenteral use is effected, for example, in the form of injection (intramuscular, subcutaneous, intravenous or by implants).

Formulations for administration via the feed or drinking water should be emphasized in particular. The active compounds can in this way be added to the feed directly or in the form of premixes or feed concentrates.

The feed includes individual feedstuffs of vegetable origin, such as hay, beet, cereals and cereal by-products, molasses and silage, individual feedstuffs of animal origin, such as meat, fats, milk products, bone-meal and fish products, and individual feedstuffs such as vitamins, proteins, sugars, starch, flours, amino acids, for example DL-methionine, and salts, such as lime and sodium chloride. The feed also includes supplement, ready-made and mixed feedstuffs. These contain individual feedstuffs in a composition which guarantees balanced nutrition in respect of energy and protein supply and the supply of vitamins, mineral salts and trace elements.

Premixes and feed concentrates are mixtures of the active compound with carriers and if appropriate other auxiliaries. The carriers include all the individual feedstuffs or mixtures thereof.

The active compounds can be present in the formulations by themselves or as a mixture with other yield-promoting active compounds, mineral feedstuffs, trace element compounds, vitamins, nitrogen-containing non-protein compounds, dyestuffs, antioxidants, aroma substances, emulsifiers, flow control auxiliaries, preservatives and pressing auxiliaries.

Other yield-promoting active compounds are, for example, antibiotics, such as tylosin and virginiamycin.

Mineral feedstuffs are, for example, dicalcium phosphate, magnesium oxide and sodium chloride.

Trace element compounds are, for example, iron fumarate, sodium iodide, cobalt chloride, copper sulphate, zinc oxide and selenium compounds.

Vitamins are, for example, vitamin A, vitamin $D_3$ and vitamin E.

Nitrogen-containing non-protein compounds are, for example, biuret and urea.

Dyestuffs are, for example, carotinoids, such as canthaxidine, zeaxanthine and capsanthine, or all dyestuffs which are permitted for coloring foodstuffs.

Antioxidants are, for example, ethoxyguin, butyl-hydroxy-toluene and ascorbic acid.

Aroma substances are, for example, vanillin.

Emulsifiers are, for example, esters of lactic acid and lecithin.

Flow control auxiliaries are, for example, sodium stearate, calcium stearate, silicic acids, bentonites and lignin-sulphonates.

Preservatives are, for example, propionic acid, calcium propionate, sorbic acid and ascorbic acid.

Pressing auxiliaries are, for example, ligninsulphonates and cellulose ethers.

The concentration of the active compounds in the feed is usually about 0.001–500 ppm, preferably 0.1–50 ppm.

The concentration of the active compounds in the premixes or feed concentrates is about 0.5 to 50 percent by weight, preferably 1 to 20 percent by weight.

The amount of active compounds administered to the animals for achieving the desired effect can be varied widely because of the favorable properties of the active compounds. It is preferably about 0.001 to 50 mg/kg, in particular 0.01 to 5 mg/kg of body weight per day. The appropriate amount of the active compound and the appropriate duration of administration depend, in particular, on the species, age, sex, state of health and nature of housing and feeding of the animals and can easily be determined by any expert.

The active compounds are administered to the animals by the customary methods. The nature of the administration depends, in particular, on the species, behaviour and state of health of the animals.

The active compounds can be administered once. However, the active compounds can also be administered temporarily or continuously during the entire or during part of the growth and yield phase. In the case of continuous administration, they can be used once or several times daily at regular or irregular intervals.

Example of the composition of a chick-rearing feed containing active compound according to the invention: 200 g of wheat, 340 g of corn, 361 g of shredded soy beans, 60 g of beef tallow, 15 g of dicalcium phosphate, 10 g of calcium carbonate, 4 g of iodinated sodium chloride, 7.5 g of a vitamin-mineral mixture of the composition given below and 2.5 g of an active compound premix of the composition given below give, after thorough mixing, 1 kg of feed.

One kg of vitamin-mineral mixture contains: 600 I.U. of vitamin A, 100 I.U. of vitamin $D_3$, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$ in cereal flour as the carrier.

1 kg of active compound premix contains 100 g of active compound and 900 g of wheat flour.

Example of the composition of a pig-rearing feed containing active compound according to the invention: 630 g of shredded cereal feed (composed of 200 g of maize, 150 g of shredded barley, 150 g of shredded oats and 130 g of shredded wheat), 80 g of fishmeal, 60 g of shredded soy beans, 60 g of tapioca flour, 38 g of brewer's yeast, 50 g of a vitamin-mineral mixture (composition as for the chick feed) 30 g of linseed cake, 30 g of maize gluten feed, 10 g of soya oil, 10 g of sugar cane molasses and 2 g of an active compound premix of the composition shown below give, after thorough mixing, 1 kg of feed.

1 kg of active compound premix contains 200 g of active compound, 20 g of vegetable oil and 780 g of calcium carbonate powder.

Example of the composition of a cattle feed containing the active compound according to the invention: 69.95% of shredded cereal feed, 10% of ground corn cobs, 8% of soy bean flour, 5% of lucerne flour, 5% of molasses, 0.6% of urea, 0.5% of calcium phosphate, 0.5% of calcium carbonate, 0.3% of sodium chloride, 0.15% of a vitamin-mineral mixture and 0.2% of an active compound premix of the composition as given for the pig feed. The vitamin-mineral mixture contains, per kg, 70,000 i.U. of vitamin A, 70,000 i.U. of vitamin $D_3$, 100 mg of vitamin E, 50 mg of $MnSO_4 \times H_2O$ and 30 mg of $ZnSO_4 \times 7H_2O$ in cereal flour as the carrier.

The active compound premix is admixed to the vitamin-mineral mixture in the required amount and this mixture is then mixed thoroughly with the remaining constituents.

EXAMPLE A

Rat feeding experiment

Female laboratory rats weighing 90–110 g of the SPF Wistar type (bred by Hagemann) are fed ad libitum with standard rat food to which the desired amount of active compound is added. Each experimental set-up is carried out with food of an identical batch, so that differences in the composition of the food cannot impair the comparability of the results.

The rats are given water ad libitum.

Each experimental group is composed of 12 rats which are fed with food to which the desired amount of active compound is added. A control group receives food without active compound. The average body weight and the scatter in the body weights of the rats is the same in each experimental group, so that comparability of the experimental groups with one another is ensured.

The weight increase and amount of perirenal fatty tissue are determined during the 13-day experiment.

The results which can be seen from the table are obtained:

TABLE A

| Rat feeding experiment | | | |
|---|---|---|---|
| Active compound Example | Dose ppm | Number of animals | Additional growth (in relation to the control) |
| Control | 25 | 12 | 100 |
| Cpd. 16 | 25 | 12 | 118 |
| Cpd. 1 | 25 | 12 | 126 |
| Cpd. 10 | 25 | 12 | 125 |
| Cpd. 1 (mixture) | 25 | 12 | 132 |

PREPARATION EXAMPLES

EXAMPLE 1

2-(3,5-Dichloro-4-amino-phenyl)-2-hydroxy-N-(1-methyl-2-methoxy-ethyl)-ethylamine

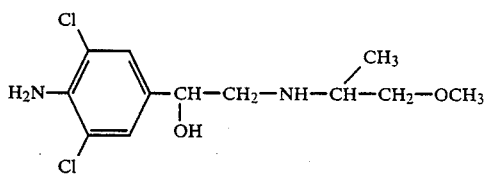

33 g of 4-amino-3,5-dichloro-ω-(1-methyl-2-methoxyethylamino)-acetophenone hydrochloride are dissolved in 180 ml of methanol and 83 ml of water, and a solution of 7.6 g of sodium borohydride in 30 ml of water is added dropwise, the pH being kept between 3 and 7 by addition of approximately 10% strength hydrochloric acid. When the reaction has ended, the mixture is rendered strongly acid and is concentrated. The concentrate is rendered basic with ammonia and extracted with ethyl acetate and the ethyl acetate phase is washed twice with water, dried and concentrated. The crystals obtained are stirred with heptane and filtered off with suction. 30.4 g of colorless crystals of melting point: 90°–95° C. are obtained.

Diastereomer mixture

By redissolving and precipitating from ethyl acetate, the pure diastereomers A and B are obtained from the diastereomer mixture and are characterized with the aid of the signals of the methoxy groups in the $^1$H-NMR spectrum. The signals, which are concentration-dependent in chloroform, are at 3.3–3.4 ppm. The signal (at higher frequencies/lower field) is attributed to diastereomer A, melting point 111°–112° C.

The following compounds were prepared analogously to Example 1:

$$H_2N-\underset{R^5}{\overset{R^4}{\bigcirc}}-\underset{OH}{CH}-\underset{R}{CH}-NH-R^{11}$$

| Cpd. No. | R | R$^4$ | R$^5$ | R$^{11}$ | m.p. [°C.] |
|---|---|---|---|---|---|
| 2 | H | Cl | Cl | CH(CH$_3$)CH$_2$—OC$_2$H$_5$ | |
| 3 | H | Cl | Cl | CH(CH$_3$)—(tetrahydrofuran-2-yl) | 110–120 |
| 4 | H | Cl | Cl | CH(CH$_3$)—(2-methyltetrahydrofuran-2-yl) | 75–80 |
| 5 | H | Cl | Cl | CH(CH$_3$)—(4-methoxycyclohexyl) | |
| 6 | H | Cl | Cl | CH(CH$_3$)—(3-methoxycyclohexyl) | |
| 7 | H | Cl | Cl | CH(CH$_3$)—(2-methoxycyclohexyl) | |
| 8 | H | Cl | Cl | CH(CH$_3$)—(3-methyloxetan-3-yl) | |
| 9 | H | Cl | Cl | CH(CH$_3$)—(oxetan-2-yl) | |

-continued $$\underset{R^5}{\overset{R^4}{\underset{H_2N}{\bigcirc}}}-\underset{OH}{\overset{}{CH}}-\underset{R}{\overset{}{CH}}-NH-R^{11}$$

| Cpd. No. | R | $R^4$ | $R^5$ | $R^{11}$ | m.p. [°C.] |
|---|---|---|---|---|---|
| 10 | H | Cl | Cl | CH(CH₃)–(tetrahydropyran-2-yl) | oil |
| 11 | H | Cl | Cl | CH(CH₃)–(tetrahydropyran-4-yl) | 133 |
| 12 | H | Cl | Cl | CH(CH₃)–CH₂–(tetrahydropyran-3-yl) | oil |
| 13 | CH₃ | Cl | Cl | CH(CH₃)CH₂—OCH₃ | |
| 19 | H | Cl | CF₃ | CH(CH₃)CH₂—OCH₃ | |
| 15 | H | Cl | CF₃ | CH(CH₃)–(tetrahydropyran-3-yl) | |
| 16 | H | Cl | CF₃ | CH(CH₃)–CH₂–(tetrahydropyran-3-yl) | |
| 17 | H | Cl | CF₃ | CH(CH₃)–(tetrahydropyran-2-yl) | |
| 18 | H | Cl | CF₃ | CH(CH₃)–(4-methoxycyclohexyl) | |
| 19 | H | Cl | H | CH(CH₃)CH₂—OCH₃ | |
| 20 | H | Cl | H | CH(CH₃)–CH₂–(tetrahydropyran-3-yl) | |
| 21 | H | Cl | H | CH(CH₃)–(tetrahydropyran-3-yl) | |
| 22 | H | Cl | H | CH(CH₃)–CH₂–(tetrahydropyran-3-yl) | |
| 23 | H | Cl | H | CH(CH₃)–(4-methoxycyclohexyl) | |

-continued

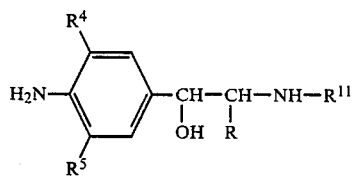

| Cpd. No. | R | R⁴ | R⁵ | R¹¹ | m.p. [°C.] |
|---|---|---|---|---|---|
| 24 | H | CN | H | CH(CH₃)CH₂—OCH₃ | |
| 5 | H | CN | H | CH(CH₃)-[tetrahydropyran-4-yl] | |
| 6 | H | CN | H | CH(CH₃)-[tetrahydropyran-3-yl] | |
| 7 | H | CN | H | CH(CH₃)-[tetrahydropyran-2-yl] | |
| 8 | H | CN | H | CH(CH₃)-[4-methoxycyclohexyl] | |
| 9 | H | Cl | CH₃ | CH(CH₃)CH₂—OCH₃ | |
| 30 | H | Cl | CH₃ | CH(CH₃)-[tetrahydropyran-4-yl] | |
| 1 | H | Cl | CH₃ | CH(CH₃)-[tetrahydropyran-3-yl] | |
| 2 | H | Cl | CH₃ | CH(CH₃)-[tetrahydropyran-2-yl] | |
| 3 | H | Cl | CH₃ | CH(CH₃)-[4-methoxycyclohexyl] | |
| 4 | H | CH₃ | CH₃ | CH(CH₃)CH₂—OCH₃ | |
| 5 | H | CH₃ | CH₃ | CH(CH₃)-[tetrahydropyran-4-yl] | |
| 6 | H | CH₃ | CH₃ | CH(CH₃)-[tetrahydropyran-3-yl] | |

-continued

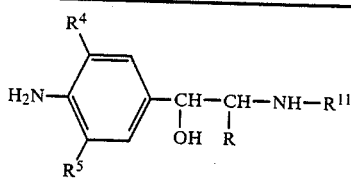

| Cpd. No. | R | R⁴ | R⁵ | R¹¹ | m.p. [°C.] |
|---|---|---|---|---|---|
| 7 | H | CH₃ | CH₃ | CH(CH₃)–[tetrahydropyran-3-yl] | |
| 8 | H | CH₃ | CH₃ | CH(CH₃)–[4-methoxycyclohexyl] | |
| 9 | H | Cl | F | CH(CH₃)CH₂—OCH₃ | |
| 40 | H | Cl | F | CH(CH₃)–[tetrahydropyran-4-yl] | |
| 1 | H | Cl | F | CH(CH₃)–[tetrahydropyran-3-yl] | |
| 2 | H | Cl | F | CH(CH₃)–[tetrahydropyran-2-yl] | |
| 3 | H | Cl | F | CH(CH₃)–[4-methoxycyclohexyl] | |
| 4 | H | CH₃ | H | CH(CH₃)CH₂—OCH₃ | |
| 5 | H | CH₃ | H | CH(CH₃)–[tetrahydropyran-2-yl] | |
| 6 | H | Cl | Cl | CH(CH₃)—C(CH₃)₂—O—CH₃ | 118–120° C. |
| 7 | H | CH₃ | H | CH(CH₃)–[tetrahydropyran-4-yl] | |
| 8 | H | H₃CHO | CH₃ | CH(CH₃)—CH₂—OCH₃ | |
| 9 | H | H₃CO | H | CH(CH₃)–[tetrahydropyran-2-yl] | |
| 50 | H | H₃CO | H | CH(CH₃)–[tetrahydropyran-3-yl] | |

-continued

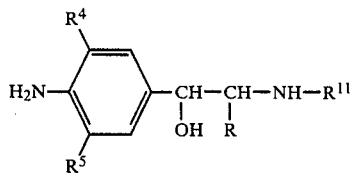

| Cpd. No. | R | R⁴ | R⁵ | R¹¹ | m.p. [°C.] |
|---|---|---|---|---|---|
| 1 | H | Cl | Cl | CH(CH₃)—CH₂—SCH₃ | |

EXAMPLE 2

2-(3,5-Dichloro-4-amino-phenyl)-2-(2,2-dimethyl-propyldimethylsilyloxy)-N-(1-methyl-2-methoxyethylamine)-ethylamine

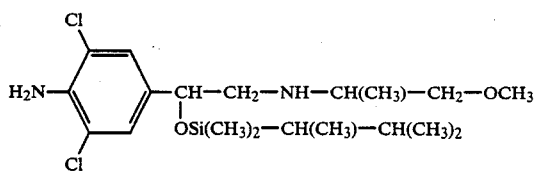

2.93 g (0.01 mol) of the compound of Example 1 are added to 1.36 g (0.02 mol) of imidazole in 15 ml of absolute dimethylformamide. 1.8 g of dimethyl-1,2-dimethyl-propyl-silyl chloride are now added at 0° to 5° C. The mixture is stirred for 2 hours, while cooling with ice, and is concentrated, the residue is taken up in toluene/water, the phases are separated, the toluene phase is washed 4 times with water, dried and concentrated and the residue is freed from residues of solvent using an oil pump. 4.3 g of an almost colorless oil are obtained.

The following silyloxy compounds are prepared by a corresponding procedure:

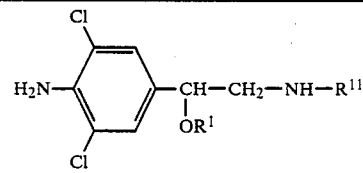

| Cpd. No. | R¹ | R¹¹ |
|---|---|---|
| 53 | Si(CH₃)₃ | CH(CH₃)CH₂OCH₃ |
| 54 | Si(CH₃)₂—C(CH₃)₃ | CH(CH₃)CH₂OCH₃ |

| Cpd. No. | R¹⁰ | R¹¹ |
|---|---|---|
| 55 | Si(CH₃)₂—CH(CH₃)—CH(CH₃)₂ | CH(CH₃)CH₂OC₂H₅ |
| 6 | Si(CH₃)₃ | CH(CH₃)CH₂OC₂H₅ |
| 7 | Si(CH₃)₂—C(CH₃)₃ | CH(CH₃)CH₂OC₂H₅ |
| 8 | Si(CH₃)₂—CH(CH₃)—CH(CH₃)₂ | 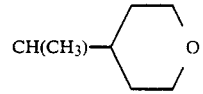 |
| 9 | Si(CH₃)₃ | 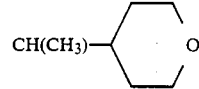 |
| 60 | Si(CH₃)₂—C(CH₃)₃ | 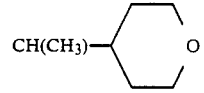 |
| 1 | Si(CH₃)₂—CH(CH₃)—CH(CH₃)₂ | 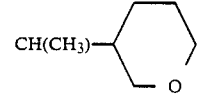 |
| 2 | Si(CH₃)₃ | 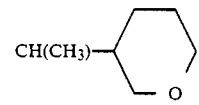 |

-continued
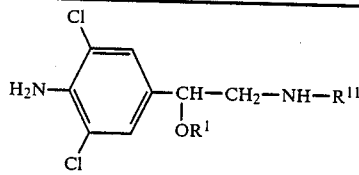
| | | | |
|---|---|---|---|
| 3 | Si(CH$_3$)$_2$—C(CH$_3$)$_3$ | 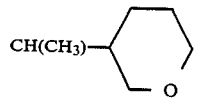 | |
| 4 | Si(CH$_3$)$_2$—CH(CH$_3$)—CH(CH$_3$)$_2$ | 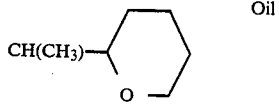 | Oil |
| 5 | Si(CH$_3$)$_3$ | 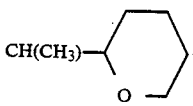 | |
| 6 | Si(CH$_3$)$_2$—C(CH$_3$)$_3$ | 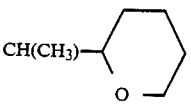 | |
| 7 | Si(CH$_3$)$_2$—CH(CH$_3$)—CH(CH$_3$)$_2$ | 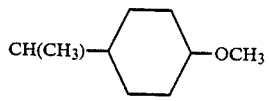 | |
| 8 | Si(CH$_3$)$_3$ | 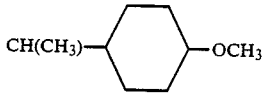 | |
| 9 | Si(CH$_3$)$_2$—C(CH$_3$)$_3$ | 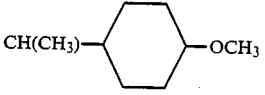 | |
| 70 | Si(CH$_3$)$_2$—CH(CH$_3$)—CH(CH$_3$)$_2$ | 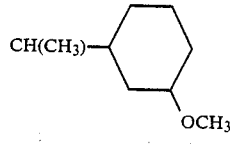 | |
| 1 | Si(CH$_3$)$_3$ | 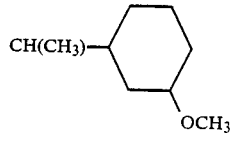 | |
| 2 | Si(CH$_3$)$_2$—C(CH$_3$)$_3$ | 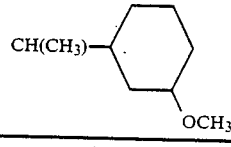 | |
EXAMPLE 3
2-(3,5-Dichloro-4-amino-phenyl)-2-acetoxy-N-(1-methyl-2-methoxy-ethyl)-ethylamine (73)

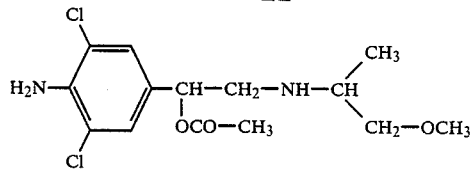

3 g of triethylamine are added to 2.93 g (0.01 mol) of 2-(3,5-dichloro-4-amino-phenyl)-2-hydroxy-N-(1-methoxy-ethyl)-ethylamine (Example 1), dissolved in 50 ml of $CHCl_3$, 1.1 g (0.011 mol) of acetic anhydride are added dropwise at $-5°$ C. and the mixture is warmed to room temperature for 2 hours. When the reaction has ended (control by thin layer chromatography), the mixture is evaporated in vacuo, the residue is taken up in ethyl acetate, the solution is washed with sodium bicarbonate solution and then with saturated sodium chloride solution, the organic phase is evaporated and the residue is chromatographed on a silica gel column (hexane/ethyl acetate=2:1). Yield: 2.5 g.

The following esters are obained by a corresponding procedure:

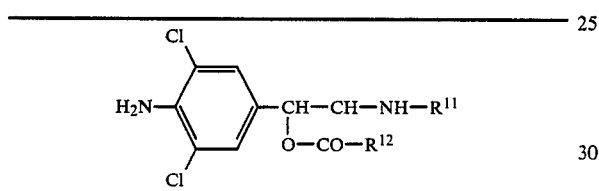

| Cpd. No. | $R^{11}$ | $R^{12}$ |
|---|---|---|
| 74 | $C_2H_5$ | $CH(CH_3)CH_2OCH_3$ |
| 5 | $CH(CH_3)_2$ | $CH(CH_3)CH_2OCH_3$ |
| 6 | $C_4H_9$ | $CH(CH_3)CH_2OCH_3$ |
| 7 | $C_6H_5$ | $CH(CH_3)CH_2OCH_3$ |
| 8 | $CH_2C_6H_5$ | $CH(CH_3)CH_2OCH_3$ |
| 9 | $CH_3$ | $CH(CH_3)CH_2OC_2H_5$ |
| 80 | $C_2H_5$ | $CH(CH_3)CH_2OC_2H_5$ |
| 1 | $CH(CH_3)_2$ | $CH(CH_3)CH_2OC_2H_5$ |
| 2 | $C_4H_9$ | $CH(CH_3)CH_2OC_2H_5$ |
| 3 | $C_6H_5$ | $CH(CH_3)CH_2OC_2H_5$ |
| 4 | $CH_2C_6H_5$ | $CH(CH_3)CH_2OC_2H_5$ |
| 5 | $CH_3$ | 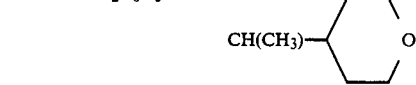 |
| 6 | $C_2H_5$ |  |
| 7 | $CH(CH_3)_2$ |  |
| 8 | $C_4H_9$ | 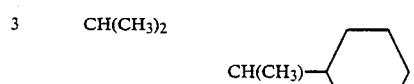 |
| 9 | $C_6H_5$ |  |

-continued

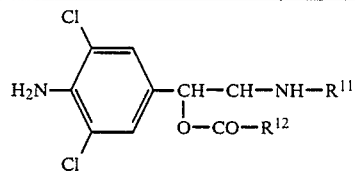

| Cpd. No. | $R^{11}$ | $R^{12}$ |
|---|---|---|
| 90 | $CH_2C_6H_5$ |  |
| 1 | $CH_3$ |  |
| 2 | $C_2H_5$ | |
| 3 | $CH(CH_3)_2$ | |
| 4 | $C_4H_9$ | |
| 5 | $C_6H_5$ | |
| 6 | $CH_2C_6H_5$ |  |
| 7 | $CH_3$ | 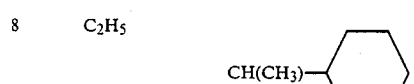 |
| 8 | $C_2H_5$ | |
| 9 | $CH(CH_3)_2$ | 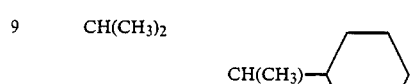 |
| 100 | $C_4H_9$ | 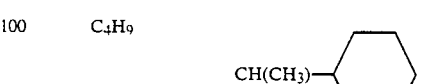 |

-continued

Structure: 3,5-dichloro-4-amino-phenyl with CH(O-CO-R¹²)-CH-NH-R¹¹

| Cpd. No. | R¹¹ | R¹² |
|---|---|---|
| 1 | $C_6H_5$ | CH(CH₃)-tetrahydropyran-2-yl |
| 2 | $CH_2C_6H_5$ | CH(CH₃)-tetrahydropyran-2-yl |
| 3 | $CH_3$ | CH(CH₃)-(4-methoxycyclohexyl) |
| 4 | $C_2H_5$ | CH(CH₃)-(4-methoxycyclohexyl) |
| 5 | $CH(CH_3)_2$ | CH(CH₃)-(4-methoxycyclohexyl) |
| 6 | $C_4H_9$ | CH(CH₃)-(4-methoxycyclohexyl) |
| 7 | $C_6H_5$ | CH(CH₃)-(4-methoxycyclohexyl) |
| 8 | $CH_2C_6H_5$ | CH(CH₃)-(4-methoxycyclohexyl) |
| 9 | $CH_3$ | CH(CH₃)-(3-methoxycyclohexyl) |
| 110 | $C_2H_5H_3)_2$ | CH(CH₃)-(3-methoxycyclohexyl) |
| 111 | $CH(CH_3)_2$ | CH(CH₃)-(3-methoxycyclohexyl) |

-continued

| Cpd. No. | R¹¹ | R¹² |
|---|---|---|
| 2 | $C_4H_9$ | CH(CH₃)-(3-methoxycyclohexyl) |
| 3 | $C_6H_5$ | CH(CH₃)-(3-methoxycyclohexyl) |
| 4 | $CH_2C_6H_5$ | CH(CH₃)-(3-methoxycyclohexyl) |

EXAMPLE 4

5-(3,5-Dichloro-4-amino-phenyl)-3-(1-methyl-2-methoxyethyl)-2-oxazolidinone

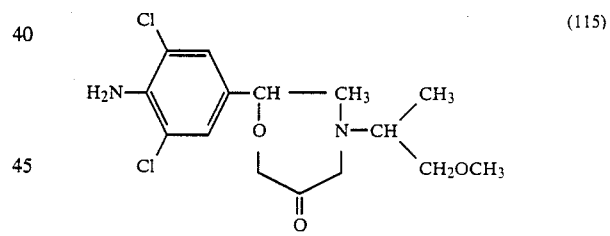

(115)

A solution of 1 g of $COCl_2$ in 20 ml of methylene chloride is added dropwise to 2.93 g (0.01 mol) of 2-(3-5-dichloro-4-amino-phenyl)-2-hydroxy-N-(1-methyl-2-methoxyethyl)-ethylamine, dissolved in 30 ml of methylene chloride and 3 g of triethylamine, at −5° C. in the course of 20 minutes. The mixture is stirred at −5° C. for 30 minutes and at room temperature for 1 hour and is evaporated in vacuo and the residue is chromatographed on a silica gel column with n-heptane/$CHCH_2$=1:1.

Yield: 1.3 g.

The following oxazolidinones are obtained in a corresponding manner:

| Cpd. No. | R11 |
|---|---|
| 116 | CH(CH3)—CH2OC2H5 |
| 7 | CH(CH3)—⟨cyclohexyl⟩—OCH3 |
| 8 | CH(CH3)—⟨cyclohexyl with OCH3⟩ |
| 9 | CH(CH3)—⟨tetrahydropyran⟩ |
| 120 | CH(CH3)—⟨tetrahydropyran⟩ |
| 1 | CH(CH3)—⟨tetrahydropyran⟩ |

| Cpd. No. | R11 | R6 | R7 |
|---|---|---|---|
| 123 | CH(CH3)CH2OCH3 | H | CH3 |
| 4 | CH(CH3)CH2OCH3 | H | C6H5 |
| 5 | CH(CH3)CH2OCH3 | CH3 | CH3 |
| 6 | CH(CH3)CH2OCH3 | CH3 | C6H5 |
| 7 | CH(CH3)—⟨tetrahydropyran⟩ | H | H |
| 8 | CH(CH3)—⟨tetrahydropyran⟩ | H | CH3 |
| 9 | CH(CH3)—⟨tetrahydropyran⟩ | H | C6H5 |
| 130 | CH(CH3)—⟨tetrahydropyran⟩ | CH3 | CH3 |
| 1 | CH(CH3)—⟨tetrahydropyran⟩ | CH3 | C6H5 |
| 2 | CH(CH3)—⟨tetrahydropyran⟩ | H | H |
| 3 | CH(CH3)—⟨tetrahydropyran⟩ | H | CH3 |
| 4 | CH(CH3)—⟨tetrahydropyran⟩ | H | C6H5 |
| 5 | CH(CH3)—⟨tetrahydropyran⟩ | CH3 | CH3 |
| 6 | CH(CH3)—⟨tetrahydropyran⟩ | CH3 | C6H5 |

EXAMPLE 5

2-(3,5-Dichloro-4-amino-phenyl)-3-(1-methyl-2-methoxyethyl)-2-oxazolidinone

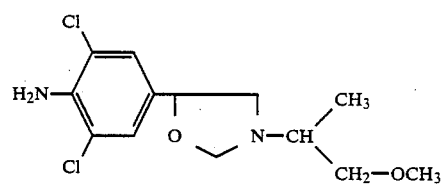

(122)

2.93 g (0.01 mol) of 2-(3,5-dichloro-4-aminophenyl)-2-hydroxy-N-(1-methyl-2-methoxy-ethyl)-ethylamine, dissolved in 60 ml of toluene, are heated with 100 ml of formaldehyde (38% strength), with the addition of 2 mg of p-toluenesulphonic acid, using a water separator, and when no further water is separated off (after about 1 hour), the mixture is cooled, washed twice with 10% strength sodium hydroxide solution and then with water and dried over Na2SO4. After evaporation, the residue is chromatographed on a silica gel column (hexane, methylene chloride=1:1) to give 2.4 g of an oil.

The following oxazolidines are obtained in a corresponding manner:

-continued

Structure: 2,6-dichloro-4-aminophenyl group with -O-C(R6)(R7)-CH2-NH-R11 substituent

| Cpd. No. | R11 | R6 | R7 |
|---|---|---|---|
| 7 | CH(CH3)-(tetrahydropyran-3-yl) | H | H |
| 8 | CH(CH3)-(tetrahydropyran-3-yl) | H | CH3 |
| 9 | CH(CH3)-(tetrahydropyran-3-yl) | H | C6H5 |
| 140 | CH(CH3)-(tetrahydropyran-3-yl) | CH3 | CH3 |
| 1 | CH(CH3)-(tetrahydropyran-3-yl) | CH3 | C6H5 |
| 2 | CH(CH3)-(4-methoxycyclohexyl) | H | H |
| 3 | CH(CH3)-(4-methoxycyclohexyl) | H | CH3 |
| 4 | CH(CH3)-(4-methoxycyclohexyl) | H | C6H5 |
| 5 | CH(CH3)-(4-methoxycyclohexyl) | CH3 | CH3 |
| 6 | CH(CH3)-(4-methoxycyclohexyl) | CH3 | C6H5 |
| 7 | CH(CH3)-(3-methoxycyclohexyl) | H | H |

-continued

| Cpd. No. | R11 | R6 | R7 |
|---|---|---|---|
| 8 | CH(CH3)-(3-methoxycyclohexyl) | H | CH3 |
| 9 | CH(CH3)-(3-methoxycyclohexyl) | H | C6H5 |
| 150 | CH(CH3)-(3-methoxycyclohexyl) | CH3 | CH3 |
| 1 | CH(CH3)-(3-methoxycyclohexyl) | CH3 | C6H5 |
| 2 | CH(CH3)-(2-methoxycyclohexyl) | H | H |
| 3 | CH(CH3)-(2-methoxycyclohexyl) | H | CH3 |
| 4 | CH(CH3)-(2-methoxycyclohexyl) | H | C6H5 |
| 5 | CH(CH3)-(2-methoxycyclohexyl) | CH3 | CH3 |

-continued

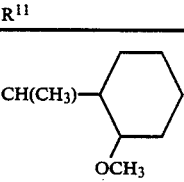

| Cpd. No. | R¹¹ | R⁶ | R⁷ |
|---|---|---|---|
| 6 |  CH(CH₃)— ...OCH₃ | CH₃ | C₆H₅ |

It is understood that the specification and examples are illustrative but not limitative of the present invention and that other embodiments within the spirit and scope of the invention will suggest themselves to those skilled in the art.

We claim:

1. An aminophenylethylamine derivative of the formula in which
   R=H or alkyl,
   R¹=acyl, aroyl, arylacyl or $$-Si\begin{matrix}R^8\\R^9\\R^{10}\end{matrix}$$

R²=methyl or ethyl,
   R³=straight-chain, branched or cyclic alkyl which is substituted by alkoxy or alkylthio or heterocyclyl which has 4–6 ring atoms and oxygen as the hetero atoms and is optionally substituted by alkyl,
   R⁴=H, alkyl (C₁-C₃), halogen, trifluoromethyl or CN,
   R⁵=alkyl (C₁-C₃), halogen, trifluoromethyl, CN, alkoxy or alkylthio,
   R⁸, R⁹ and R¹⁰=a straight-chain or branched alkyl radical.

2. A compound according to claim 1, in which
   R=H or methyl, —Si(CH₃)₂CH(CH₃)CH(CH₃)₂ or Si(CH₃)₂C(CH₃)₃,
   R² methyl,
   R³ represents the radical (CR¹¹R¹²)ₙ—X—R¹³, wherein
   R¹¹ and R¹² represent hydrogen or methyl or
   R³ represents C₅₋₆-cycloalkyl which is substituted by C₁₋₄-alkoxy,
   n represents 1, 2 or 3,
   X represents O or S, and
   R¹³ represents C₁₋₄-alkyl or, together with one of the radicals R¹¹ or R¹² and the atoms to which they are bonded, forms a 4- to 6-membered ring which is interrupted by O and is optionally substituted by methyl.

3. A compound according to claim 1, in which $$-NH-CH\begin{matrix}R^2\\R^3\end{matrix} \text{ is}$$

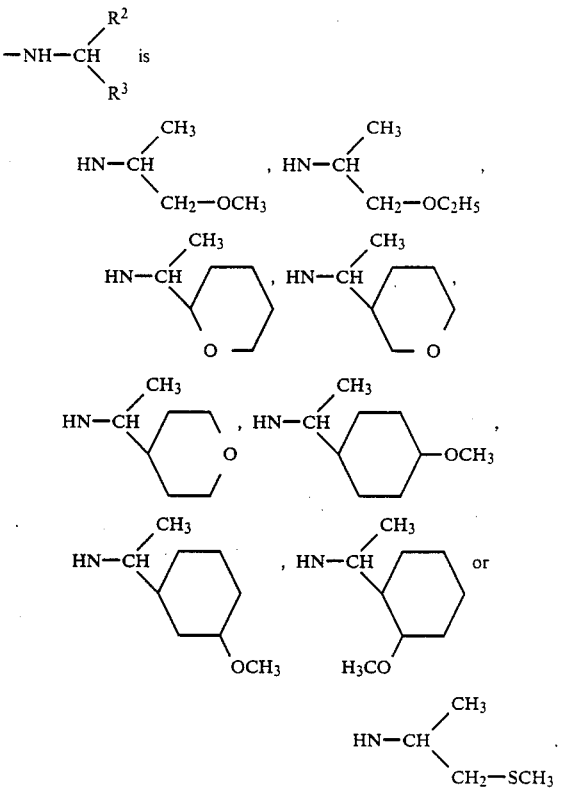

4. An animal yield-promoting composition comprising an amoumt effective therefor of a compound according to claim 1 and a diluent.

5. A method of promoting the yield of animals which comprises supplying to such animals a yield-promoting effective amount of an aminophenylethylamine derivative of the formula

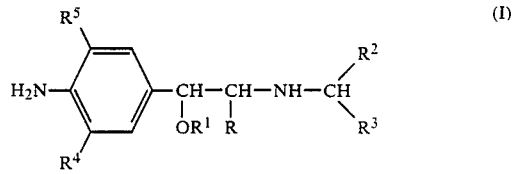 (I)

in which
   R=H or alkyl,
   R¹=hydrogen, acyl, aroyl, arylacyl or

   $$-Si\begin{matrix}R^8\\R^9\\R^{10}\end{matrix}$$

R²=methyl or ethyl,
   R³=straight-chain, branched or cyclic alkyl which is substituted by alkoxy or alkylthio or heterocyclyl which has 4–6 ring atoms and oxygen as the hetero atom and is optionally substituted by alkyl,
   R⁴=H, alkyl (C₁-C₃), halogen, trifluoromethyl or CN,
   R⁵=alkyl (C₁-C₃), halogen, trifluoromethyl, CN, alkoxy or alkylthio, and
   R⁸, R⁹ and R¹⁰=a straight-chain or branched alkyl radical.

6. The method according to claim 5, wherein such compound is 2-(3,5-dichloro-4-amino-phenyl)-2-hydroxy-N-(1-methyl-2-methoxy-ethyl)-ethylamine.

* * * * *

UNITED STATES PATENT AND TRADEMARK OFFICE
CERTIFICATE OF CORRECTION

PATENT NO. : 4,935,409

DATED : June 19, 1990

INVENTOR(S) : Wollweber et al.

It is certified that error appears in the above-identified patent and that said Letters Patent is hereby corrected as shown below:

Col. 29, lines 26-27    After " formula " insert -- 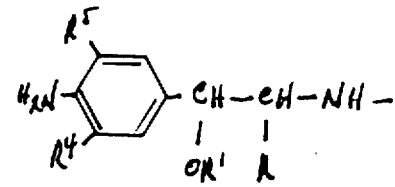

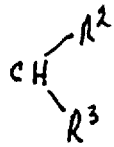

(I)--

Signed and Sealed this

First Day of September, 1992

Attest:

DOUGLAS B. COMER

Attesting Officer    Acting Commissioner of Patents and Trademarks